United States Patent [19]

Forrester

[11] Patent Number: 4,692,210
[45] Date of Patent: Sep. 8, 1987

[54] METHOD AND APPARATUS FOR MEASURING THE DISTRIBUTION OF FIBER WIDTHS AND ADJUSTING THE REFINING OF FIBROUS STOCK

[76] Inventor: Gilbert Forrester, 10/62 Alexandra Street, Hunters Hill, New South Wales, 2110, Australia

[21] Appl. No.: 789,783

[22] Filed: Oct. 21, 1985

[30] Foreign Application Priority Data

Oct. 25, 1984 [AU] Australia .............................. PG7821

[51] Int. Cl.$^4$ ........................ D21D 1/20; G01N 15/02
[52] U.S. Cl. ........................................ 162/49; 162/61; 162/254; 162/263; 356/335; 356/441; 356/442
[58] Field of Search ................. 162/49, 254, 263, 198, 162/61; 73/63; 356/440, 441, 442, 335, 238

[56] References Cited
U.S. PATENT DOCUMENTS 4,318,180 3/1982 Lundqvist et al. .................... 162/49
4,514,527 4/1985 Karlsson et al. ..................... 162/254
4,554,051 11/1985 Dunforth ........................... 162/254

Primary Examiner—Steve Alvo
Attorney, Agent, or Firm—Leydig, Voit & Mayer

[57] ABSTRACT

A method and apparatus for making paper by refining fibrous stock. The stock is passed through an adjustable refining means and a sample of the refined stock is analyzed using a fibre fineness distribution analyzer to produce, over a range of fibre widths, counts of the number of fibres in the sample which have a selected fibre width. Fibre width is plotted against fibre count at intervals of 1 μm over the range of from 7 μm to 64 μm to obtain a fibre fineness distribution curve. The fibre fineness distribution curve is compared with a reference fibre fineness distribution curve obtained by the prior analysis of stock known to have produced paper of desired quality. The refining means is then adjusted to produce a stock the analysis of which produces a distribution curve substantially the same as the reference curve.

6 Claims, 3 Drawing Figures

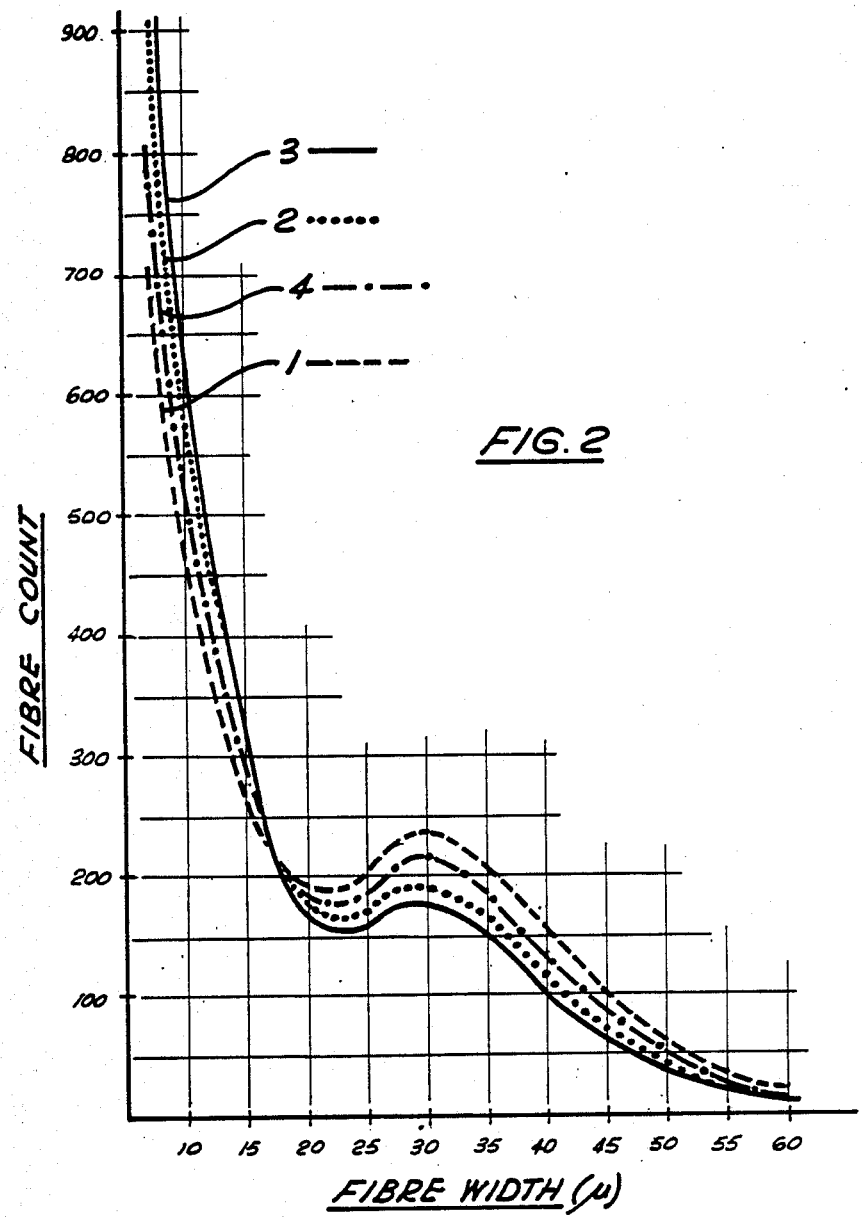

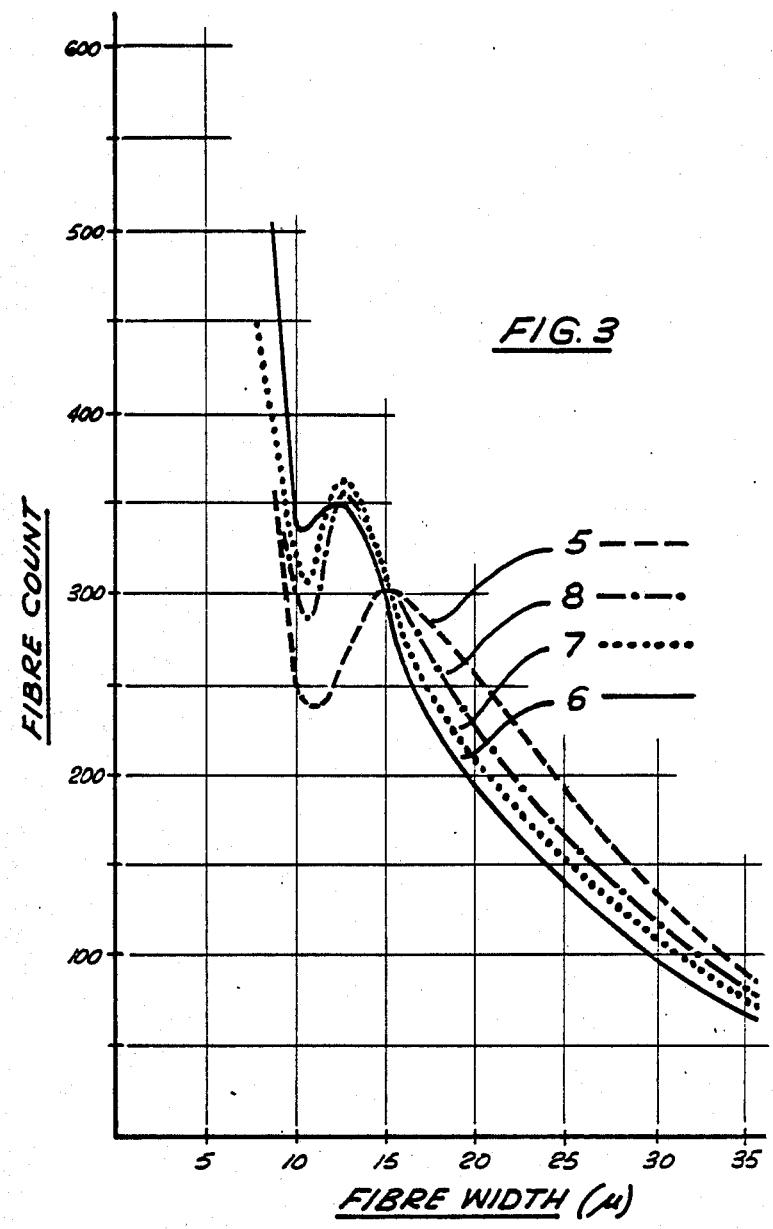

METHOD AND APPARATUS FOR MEASURING THE DISTRIBUTION OF FIBER WIDTHS AND ADJUSTING THE REFINING OF FIBROUS STOCK

BACKGROUND OF THE INVENTION

1. Field of the Invention

The present invention relates to the making of paper and paper boards and in particular, to a method and apparatus for adjusting fibre treatment apparatus to produce paper having desired qualities.

2. Description of the Prior Art

In the machine manufacture of paper and cellulose products, the paper making materials, known as "stock" usually consist of a water suspension of wood or vegetable fibres which have been separated by chemical or mechanical means. These fibres are combined with additional ingredients such as dye stuffs, alum, clay and the like, to impart the desired characteristics to the finished paper product.

Preparation of the fibre stock is a most critical processing phase, which greatly determines the quality and physical characteristics of the finished product. The properties of wood and natural fibres vary, even in the same plant species, due to differences in factors affecting growth. Other variations are introduced by the chemical and mechanical processes which reduce timber logs to individual cellulose fibres. To improve uniformity, the final preparation of the fibres prior to forming into a sheet on the paper machine is by treating the slurry of fibres in machines known as beaters and refiners. These machines typically have rotating parts faced with metal or abrasives, and corresponding fixed parts similarly faced with metal or abrasives.

During operation the rotating parts are maintained at a controlled very small spacing from the adjacent corresponding fixed metal or abrasive faced parts. The fibres are crushed by being pumped in a slurry through the spacing. The fibres which are originally relatively smooth and tubular in shape are smashed, and their exteriors develop fine fibrils which interlock or "felt" together when the slurry is formed into a sheet, contributing greatly to the strength of the finished product.

By practical experience, an optimum degree of refining is determined for any specific product. Under-refining may produce a low strength product; over-refining may affect opacity, texture and other qualities, in addition to wasting considerable energy.

Several beaters and refiners operating in parallel are required to prepare stock for a single paper machine. For practical reasons such as routine maintenance, the internal mechanical condition of the refiners will vary. For example reconditioning of the refiners is performed in sequence by shutting down a single unit while others in the parallel system continue to operate. Thus, a set of refiners feeding a single paper machine may consist of some new or freshly reconditioned units, while others are worn and ready to be reconditioned. The effect of such unequal refiners on wood fibres will vary greatly, the reconditioned machines requiring less energy input to produce the desired refining result than is required of a worn machine. The new or reconditioned machines may also tend to cut a greater proportion of fibres than will a worn machine.

To achieve the desired degree of fibre treatment, the common practice in paper mills is to control the beaters and refiners according to a predetermined energy input per ton of fibre stock, in terms of Horsepower Tons per Day. The fibre slurry is passed through the beaters or refiners until a desired horsepower per hour has been expended per ton of fibre in the system. But as noted above, a uniform energy input will not necessarily produce a uniformly treated fibre stock, as the internal condition of the machines may vary.

Hitherto, the degree of refining achieved for a particular mixture of fibres has not been able to be confirmed until the fibre has been formed into a dried sheet, samples of which are periodically subjected to a series of physical tests to check quality. To provide for uninterrupted feeding of the continuously running paper machine, yet allow for product and formulation changes, the beaters and refiners discharge into large holding tanks which are fed in sequence to the paper machine. Thus, a delay of up to several hours may occur before a batch of refined stock is formed into sheets so that the result of refining can be confirmed. If the physical tests indicate that under or over-refining has occurred, any correction made at the beaters or refiners to alter the energy input per ton of stock will not show an effect on the finished paper qulity for a long period, during which a non-standard product will continue to be made. The cost in wasted energy and possible price reduction of a lower grade product may be considerable.

It is an object of the present invention to provide a method of making paper and an apparatus for making paper in accordance with the method which will overcome, or substantially ameliorate, the abovementioned disadvantages.

SUMMARY OF THE INVENTION

According to a first aspect of the present invention there is provided a method of making paper from fibrous stock comprising the steps of passing the stock through adjustable refining means, analysing the refined stock using fibre analysing means to obtain characteristic output information, comparing the output information with reference information obtained by the prior analysis of stock known to have produced paper of a desired quality, and adjusting the refining means to produce a stock the analysis of which produces output information substantially the same as the reference information.

An apparatus for making paper from fibrous stock comprising fibre analysing means to analyse refined stock and produce characterisic output information, storage means to store reference information obtained by the prior analysis of stock known to have produced paper having a desired quality, means to compare the output information with the reference information and means responsive to the difference between the output information and reference information to adjust the refining means to produce a stock the analysis of which produces output information substantially the same as the reference information.

Preferably the fibre analysing means comprises a fibre fineness distribution analyser which produces for a range of fibre widths counts of the number of fibres in a sample which have a selected fibre width.

In a preferred form, the fibre fineness distribution analyser output information comprises a fibre fineness distribution curve obtained by plotting fibre width against fibre count over said range of fibre widths and the refining means is adjusted to produce a stock the analysis of which produces a fibre fineness distribution curve substantially the same as a reference curve obtained by analysing stock known to produce paper having desired qualities.

An embodiment of the present invention will now be described, by way of example only, with reference to the accompanying drawings.

BRIEF DESCRIPTION OF THE DRAWINGS

FIG. 2 is a plot of fibre width against fibre count for four samples of the same fibre stock, each sample having been subjected to a different refining duration; and FIG. 3 is a plot similar to FIG. 2 for a different mixture of fibres.

DESCRIPTION OF THE PREFERRED EMBODIMENT

Figure 1:
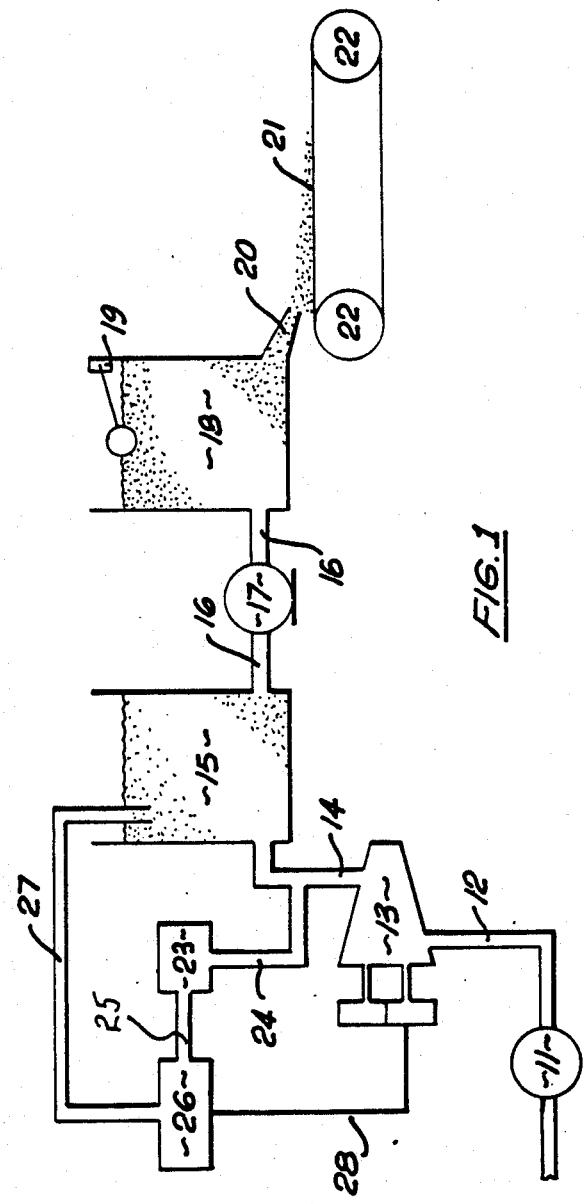
FIG. 1 is a schematic diagram of part of a paper manufacturing system.

As seen in FIG. 1, the paper manufacturing system comprises a pump 11 which pumps stock along pipe 12 through refining means 13 and into a storage chest 15 via pipe 14. The refining means 13 can be a beater or refiner as described above or any other suitable known means.

From chest 15 the stock is pumped by pump 17 via pipes 16 to a feed tank 18. The level of stock in the tank 18 is controlled by a float valve 19. The stock feeds from the bottom of tank 18 via nozzle 20 onto a continuous wire gauze belt 21 driven around rollers 22. Movement of the belt 21 causes the stock to form a thin layer on the belt 21. The thin layer is dried by being passed around heated surfaces to become paper or paper board.

A sampling device 23 is connected by sampling tube 24 to pipe 14 on the downstream side of refining means 13. The sampling device 23 continuously removes a small sample of the stock from pipe 14 and pumps the sample via tube 25 to fibre analysing means 26 comprising a fibre fineness distribution analyser model FDA 200 manufactured by Information Electronics Ltd of Canberra, Australia.

The fibre fineness distribution analyser (not shown) is characterized by a narrow tube or channel through which a sample of the papermaking fibre slurry flows, and a laser optics arrangement which views the slurry through a transparent section of the channel. Typically, the transparent section has parallel optically flat sides enclosing a narrow passage, the laser beam is arranged to penetrate transversely through both sides of the channel and the contained fiber slurry, to impinge upon a laser target on the opposite side of the channel.

The laser beam and target are arranged to view a circular area of the flow channel, the circle having a diameter substantially less than the average length of the fibres to be viewed. A complementary electronic system is arranged to generate a signal at the instant of maximum obscuring of the laser target by an intervening fiber. Since the diameter of the viewing circle is fixed, the length of any observed fibre is that of the circle diameter, and the magnitude of the signal generated will vary in proportion to the area of the target which has been obscured by the fibre, and the signal may then be computed in terms of the fibre width, or fineness. In further refinement of the fiber fineness distribution analyser, the circular viewing area is divided into two halves, the dividing line being parallel to the flow direction, thus forming the viewing "window" into two semi-circular halves. The laser target is similarly arranged to generate a separate signal from each semi-circular area of the viewing window.

In the corresponding electronic measuring system, a fibre must obscure an equal area of each semi-circular target and thus generate two equal simultaneous electronic signals in order for its measured width to be accepted for recording purposes.

If the electronic signals corresponding to the two semi-circular areas are not equal, it is because a fibre is only partly across the viewing window, or because more than one fibre is passing the laser optics. Such signals may be erroneous, and are not accepted for recording purposes. In practice, fibres accepted for recording comprise 20%–35% of total fibres viewed.

This apparatus produces for a range of fibre widths counts of the number of fibres in a sample which have a selected fibre width. A fibre fineness distribution curve is obtained by plotting fibre width against fibre count. Preferably, the range of fibre widths is from 7 $\mu$m to 64 $\mu$m and fibre count is plotted at increments of 1 $\mu$m. After analysis the sample is discharged via tube 27 to storage chest 15.

The fibre fineness distribution curve is compared with a stored reference curve obtained by analysing stock known to produce paper having the desired qualities. A correction signal determined by the difference in the measured curve and the reference curve is generated by fibre analysing means 26 and transmitted via line 28 to adjust refining means 13. The analysing means 26 continues to generate a correction signal until the fibre fineness distribution curve of the stock being measured is substantially the same as the reference curve.

FIG. 2 is a plot of fibre width against fibre count for four samples of fibre. The test samples were pure unbleached spruce fibres, prepared by kraft process and separately refined in the same beater for the beating times tabulated below.

| Sample No. | Beating Time (minutes) | Equivalent Energy Input (Horsepower Tons/day) |
|---|---|---|
| 1 | 0 | 0 |
| 4 | 10 | 2.84 |
| 2 | 20 | 5.53 |
| 3 | 45 | 12.72 |

The fibre fineness distribution of each sample for fibres having a fineness or apparent width between 7 $\mu$m and 64 $\mu$m was measured using the FDA 200 analyser in accordance with normal operating procedure. The measurements were conducted using 10,000 counted fibres and repeated several times, the results averaged and plotted to obtain FIG. 2. The lines marked 1,2,3,4, correspond to the sample numbers used in the above table.

FIG. 3 is a similar plot of measurements conducted on four samples of a mixture of spruce and fir fibres, each sample having been subjected to refining times tabulated below.

| Sample No. | Refining Time (minutes) |
|---|---|
| 5 | 0 |
| 8 | 10 |
| 7 | 20 |
| 6 | 45 |

The lines marked 5, 6, 7, 8 correspond to sample numbers used in the above table.

These lines are the fibre fineness distribution curves of the samples and the present invention is founded on the discovery or appreciation that each curve is uniquely related to the degree of refining of the particular fibre or mixture of fibres and to the paper making quality of the sample from which it is derived. By recording fibre fineness distribution curves of samples of stock and the qualities of the paper produced from the same stock it is possible to obtain the abovementioned reference curves corresponding to stock known to produce paper having desired qualities.

It will be apparent that the present invention, by providing for the sampling and assessment of stock immediately after refining, allows rapid adjustment of optimum fibre refining to obtain a uniform paper product of desired quality.

The foregoing describes only one embodiment of the present invention and modifications may be made thereto by persons skilled in the art without departing from the scope of the present invention.

I claim:

1. A method of making paper of a selected quality from a type of fibrous stock, said method comprising the steps of refining the stock, analysing the refined stock to produce a measurement of the distribution of fibre widths over a selected range of fibre widths, comparing said measurement with a reference measurement of the distribution of fibre widths over said selected range of fibre widths obtained from a prior analysis of the same type of stock refined to a degree known to produce paper of said selected quality, and adjusting the refining of the stock to produce a stock the analysis of which produces a measurement of the distribution of fibre widths substantially the same as said reference measurement.

2. A method as claimed in claim 1 wherein said measurement comprises counts of the number of fibres in a sample which have a selected fibre width.

3. A method as claimed in claim 1 wherein said measurement comprises a fibre fineness distribution curve obtained by plotting fibre width against counts of the number of fibres in a sample which have a selected width.

4. A method as claimed in claim 3 wherein said selected range of fibre widths is from 7 $\mu$m to 64 $\mu$m and fibre count is plotted at intervals of 1 $\mu$m.

5. A method as claimed in claim 1 further comprising the step of adjusting the refining of said stock by using a correction signal determined by the difference between said measurement and said reference measurement.

6. An apparatus for making paper of a selected quality from a type of fibrous stock, said apparatus comprising adjustable refining means to produce refined stock, a fibre fineness distribution analyser to produce a measurement of the distribution of fibre widths over a selected range of fibre widths in a sample of the refined stock, storage means to store a reference measurement of the distribution of fibre widths over said selected range of fibre widths obtained from a prior analysis of the same type of stock refined to a degree known to produce paper of said selected quality, means to compare said measurement with said reference measurement, and means responsive to the difference between said measurement and said reference measurement to adjust the refining means to produce a stock the analysis of which produces a measurement of the dstribution of fibre widths substantially the same as said reference measurement.

* * * * *